US010081851B2

(12) United States Patent
Matsuoka et al.

(10) Patent No.: US 10,081,851 B2
(45) Date of Patent: Sep. 25, 2018

(54) METHOD FOR RECOVERING HIGH-PURITY SCANDIUM

(71) Applicant: SUMITOMO METAL MINING CO., LTD., Tokyo (JP)

(72) Inventors: Itsumi Matsuoka, Niihama (JP); Hidemasa Nagai, Niihama (JP); Keiji Kudo, Niihama (JP); Shin-ya Matsumoto, Niihama (JP); Tatsuya Higaki, Niihama (JP); Yoshitomo Ozaki, Niihama (JP); Hirofumi Shouji, Niihama (JP); Hiroshi Kobayashi, Niihama (JP)

(73) Assignee: SUMITOMO METAL MINING CO., LTD., Tokyo (JP)

( * ) Notice: Subject to any disclaimer, the term of this patent is extended or adjusted under 35 U.S.C. 154(b) by 0 days.

(21) Appl. No.: 15/526,862

(22) PCT Filed: Nov. 25, 2015

(86) PCT No.: PCT/JP2015/083020
§ 371 (c)(1),
(2) Date: May 15, 2017

(87) PCT Pub. No.: WO2016/084830
PCT Pub. Date: Jun. 2, 2016

(65) Prior Publication Data
US 2017/0321301 A1 Nov. 9, 2017

(30) Foreign Application Priority Data

Nov. 26, 2014 (JP) ................................. 2014-239086
Nov. 25, 2015 (JP) ................................. 2015-229343

(51) Int. Cl.
C22B 59/00 (2006.01)
C01F 17/00 (2006.01)
C22B 1/02 (2006.01)
C22B 3/28 (2006.01)
C22B 3/42 (2006.01)
C22B 3/44 (2006.01)
C22B 3/08 (2006.01)
C07C 51/41 (2006.01)

(52) U.S. Cl.
CPC .............. C22B 59/00 (2013.01); C01F 17/00 (2013.01); C01F 17/0043 (2013.01); C07C 51/412 (2013.01); C22B 1/02 (2013.01); C22B 3/001 (2013.01); C22B 3/08 (2013.01); C22B 3/42 (2013.01); C22B 3/44 (2013.01); C01P 2006/80 (2013.01); Y02P 10/234 (2015.11)

(58) Field of Classification Search
CPC .. C22B 59/00; C22B 3/08; C22B 3/42; C22B 3/44; C22B 1/02; C01F 17/0043
USPC ..................... 423/21.5, 21.1, 263
See application file for complete search history.

(56) References Cited

U.S. PATENT DOCUMENTS

| 4,626,280 A * | 12/1986 | Vanderpool ......... C01F 17/0006 423/147 |
| 4,718,995 A | 1/1988 | Vanderpool et al. |
| 4,765,909 A * | 8/1988 | Rourke ................. C01F 15/00 210/672 |
| 5,787,332 A * | 7/1998 | Black ..................... C22B 1/06 423/16 |
| 7,282,187 B1 * | 10/2007 | Brown .................. C22B 3/001 423/10 |
| 9,399,804 B2 | 7/2016 | Ozaki et al. |
| 2012/0207656 A1 * | 8/2012 | Duyvesteyn ............ C22B 1/04 423/21.1 |
| 2014/0154155 A1 | 6/2014 | Wyrsta et al. |
| 2016/0047014 A1 | 2/2016 | Ozaki et al. |

FOREIGN PATENT DOCUMENTS

| CA | 2890572 A1 | 11/2014 |
| CN | 103361486 A | 10/2013 |
| CN | 103468978 A | 12/2013 |
| JP | 03-173725 A | 7/1991 |
| JP | 09-194211 A | 7/1997 |
| JP | 09-248463 A | 9/1997 |
| JP | 09-291320 A | 11/1997 |
| JP | 2004-256470 A | 9/2004 |
| JP | 2016-065273 A | 4/2016 |
| WO | 2014/110216 A1 | 7/2014 |

(Continued)

OTHER PUBLICATIONS

International Search Report dated Feb. 16, 2016, issued for PCT/JP2015/083020.
Extended European search report issued to EP Patent Application No. 15863799.1, dated Sep. 15, 2017.
Zhong Xueming et al., "Technology of Extracting Scandium Oxide by primary Amine," Chinese Journal of Rare Metals, vol. 26, No. 6, Nov. 2002, pp. 527-529 and a partial translation thereof. (cited in the Nov. 3, 2017 CN OA).
Weiwei Wang et al., "Separation and purification of scandium by solvent extraction and related technologies: a review" Journal of Chemical Technology and Biotechnology, vol. 86, pp. 1237-1246, Published online in Wiley Online Library: May 27, 2011. (cited in the Jul. 21, 2017 AU OA).

(Continued)

Primary Examiner — Steven J Bos
(74) Attorney, Agent, or Firm — Locke Lord LLP

(57) ABSTRACT

Provided is a method for recovering scandium, with which it is possible to easily and efficiently recover high-purity scandium from nickel oxide ores. This method for recovering scandium involves passing a solution containing scandium through an ion exchange resin, then subjecting the eluant eluted from the ion exchange resin to solvent extraction and separating the extraction residual liquid and the extraction agent after extraction, then performing an oxalation process on the extraction residual liquid to obtain a scandium oxalate precipitate, and roasting the precipitate to obtain scandium oxide, wherein the method is characterized in that an amine-based extraction agent is used as the extraction agent for solvent extraction.

19 Claims, 5 Drawing Sheets

(56) References Cited

FOREIGN PATENT DOCUMENTS

WO      2014/118288    *   8/2014
WO      2014/181721 A1    11/2014

OTHER PUBLICATIONS

Office Action dated Jul. 21, 2017, issued to AU Patent Application No. 2015351446.
English translation of First Office Action issued to corresponding CN Patent Application No. 2015800622820, dated Nov. 3, 2017, which was submitted in IDS dated Dec. 13, 2017.
Second Office Action issued to CN Patent Application No. 2015800622820, dated Apr. 2, 2018.

\* cited by examiner

METHOD FOR RECOVERING HIGH-PURITY SCANDIUM

TECHNICAL FIELD

The present invention relates to a method of recovering scandium. More specifically, the present invention relates to a method of simply and efficiently recovering scandium contained in nickel oxide ore, the method comprising: performing solvent extraction with an amine-based extractant.

BACKGROUND ART

Scandium is extremely valuable as an additive for high-strength alloys and an electrode material for fuel cells. However, scandium has not yet been used widely due to the small production quantity and high cost thereof.

Meanwhile, a trace amount of scandium is contained in nickel oxide ore such as laterite ore and limonite ore. However, nickel oxide ore has not been used industrially as a raw material for nickel for many years because the grade of nickel in nickel oxide ore is low. Consequently, very few studies also have been conducted for a method of industrially recovering scandium from nickel oxide ore.

Nonetheless, in recent years, the HPAL process has been emerging as a practical method, in which nickel oxide ore is introduced into a pressure vessel along with sulfuric acid, and heated at a high temperature of 240° C. to 260° C. to allow solid-liquid separation into a nickel-containing leachate and a leach residue. In the HPAL process, a neutralizing agent is added to the leachate obtained to separate impurities, and then a sulfurizing agent is added to the resulting leachate from which impurities are separated out, allowing recovery of nickel as nickel sulfide. Subsequently, this nickel sulfide may be subjected to a known nickel refinement process to obtain electrolytic nickel and nickel salt compounds.

In the HPAL processes as described above, scandium contained in nickel oxide ore will be contained in a leachate along with nickel (see Patent Document 1). Subsequently, when a neutralizing agent is added to a leachate obtained from the HPAL process to separate impurities, and a sulfurizing agent is then added, nickel is recovered as nickel sulfide while scandium remains in the acidic solution after addition of the sulfurizing agent. In this way, nickel can effectively be separated from scandium by using the HPAL process.

A method of separating scandium by using a chelating resin has also been documented (see Patent Document 2). Specifically, according to the method disclosed in Patent Document 2, nickel-containing oxide ore is first treated at high temperature and high pressure under an oxidizing atmosphere to selectively extract nickel and scandium into an acidic aqueous solution. Subsequently, the pH of the resulting acidic solution is adjusted to the range of 2 to 4, and nickel is then selectively precipitated and recovered as a sulfide by means of a sulfurizing agent. Next, the resulting solution from which nickel has been recovered is allowed to make contact with a chelating resin, and the chelating resin is washed with a dilute acid. Then, the chelating resin which has been washed is allowed to make contact with a strong acid to elute scandium from the chelating resin.

Further, as a method of recovering scandium from the aforementioned acidic solution, the method of recovering scandium by means of solvent extraction has also been proposed (see Patent Documents 3 and 4). Specifically, according to the method disclosed in Patent Document 3, an organic solvent is first added to an aqueous-phase scandium-containing solution to extract a scandium component into the organic solvent, the organic solvent comprising 2-ethylhexyl sulfonic acid-mono-2-ethylhexyl diluted with kerosene, and the aqueous-phase scandium-containing solution containing one or more of at least iron, aluminum, calcium, yttrium, manganese, chromium, and magnesium in addition to scandium. Then, in order to separate yttrium, iron, manganese, chromium, magnesium, aluminum, and calcium extracted into the organic solvent along with scandium, an aqueous solution of hydrochloric acid is added, and scrubbing is performed to remove these elements. Then, an aqueous solution of NaOH is added to the organic solvent to transform scandium remaining in the organic solvent into a slurry containing $Sc(OH)_3$, and the slurry is filtered to obtain $Sc(OH)_3$, which is then dissolved in hydrochloric acid to obtain an aqueous solution of scandium chloride. Subsequently, oxalic acid is added to the resulting aqueous solution of scandium chloride to obtain a precipitate of scandium oxalate. This precipitate is filtered to remove iron, manganese, chromium, magnesium, aluminum, and calcium into a filtrate, and then calcination is performed to obtain highly pure scandium oxide.

Moreover, Patent Document 4 describes a method of selectively separating and recovering scandium from a scandium-containing supply liquid, the method comprising: bringing the scandium-containing supply liquid into contact with an extracting agent at a certain ratio in a batch process.

The grade of scandium recovered according to these methods is known to be about 95% to 98% pure in terms of scandium oxide. The above grade may be good enough for those uses such as an additive in alloys. However, a much higher purity, for example, the purity of about 99.9%, is required as a grade used for electrolytes of fuel cells which have recently much in demand. Otherwise, their full capability may not be obtained.

However, nickel oxide ore described above contains various impurity elements such as manganese and magnesium in addition to iron and aluminum, and may even contain a trace amount of actinoid elements, such as uranium and thorium, and others although impurities may somewhat vary in identities and their contents, depending on mining regions.

The acceptable upper limit of the grade of an impurity element may be pre-determined for scandium to be used in electrolytes of fuel cells and the like as described above. Therefore, each element may need to be individually separated out to the level of the acceptable limit or below.

However, the uses of the chelating resin and the organic solvent disclosed in Patent Documents 2 and 3 may not effectively separate some of the aforementioned impurity elements, in particular actinoids, from scandium because some of the aforementioned impurity elements may show similar behaviors as scandium. Further, impurities to be contained in the leachate of nickel oxide ore, such as iron and aluminum, have much higher concentrations than scandium. Due to these large amounts of impurities and other effects, a method suitable for industrially recovering high purity scandium from nickel oxide ore has not been found.

Further, scandium is preferably recovered in a solid form in order to facilitate the use of scandium as a product. To this end, a process for obtaining precipitates of scandium hydroxide and scandium oxalate needs to be performed, the process comprising adding a neutralizing agent such as an alkaline substance; and oxalic acid to a solution containing scandium obtained by the techniques disclosed in the aforementioned Patent Documents.

However, for example, some or most of impurities such as aluminum and iron contained in the solution are also precipitated at the same time when an alkaline substance is added to recover scandium in a form of hydroxide. This makes selective separation of scandium difficult. Further, a hydroxide of scandium may disadvantageously take a gel form with inferior filterability, resulting in decreased handling properties such as long filtering time.

In contract, for example, according to the method of recovering scandium as an oxalate salt as disclosed in Patent Document 5, the method comprising: adding oxalic acid ((COOH)$_2$) to a scandium-containing solution, the resulting scandium oxalate has good filterability, showing an advantage of better handling properties.

However, the scandium-containing solution obtained from nickel oxide ore as decreased above contains a large amount of impurities such as aluminum and iron from ore components, and thus a large amount of precipitates of aluminum oxalate and ferrous oxalate (II) are also generated, again resulting in difficult recover of scandium. In addition, this process suffers from an increased cost of oxalic acid to be used.

Accordingly, an oxidizing agent is added to the scandium-containing solution to oxidize iron ions contained in the solution into a trivalent form. This promotes formation of highly soluble ferric oxalate (III), thereby preventing precipitation of iron. This process, however, suffers from an increased cost of the oxidizing agent.

As described above, effective recovery of high purity scandium from nickel oxide ore is difficult because a wide variety of impurities need to be separated out such as iron and aluminum, which are contained in large amounts, and actinoid elements.

Patent Document 1: Japanese Unexamined Patent Application, Publication No. H03-173725
Patent Document 2: Japanese Unexamined Patent Application, Publication No. H09-194211
Patent Document 3: Japanese Unexamined Patent Application, Publication No. H09-291320
Patent Document 4: PCT International Publication No. WO2014/110216
Patent Document 5: Japanese Unexamined Patent Application, Publication No. H09-248463

DISCLOSURE OF THE INVENTION

Problems to be Solved by the Invention

The present invention is made in view of the above actual circumstances. An object of the present invention is to provide a method of recovering scandium, in which high purity scandium can simply and effectively be recovered from nickel oxide ore.

Means for Solving the Problems

The present inventors have conducted extensive studies to solve the aforementioned problems. As a result, the present inventors find that high purity scandium can simply and effectively be recovered from nickel oxide ore by subjecting a scandium-containing acidic solution to solvent extraction using an amine-based extractant. Then the present invention has been completed. That is, the present invention can provide the followings.

(1) A first embodiment of the present invention provides a method of recovering scandium, comprising: passing a scandium-containing solution through an ion exchange resin; then subjecting an eluent eluted from the ion exchange resin to solvent extraction to allow separation into a raffinate liquid and an post-extraction extractant; then adding oxalic acid to the raffinate liquid to obtain a precipitate of scandium oxalate; and roasting the precipitate to obtain scandium oxide, in which an amine-based extractant is used as an extractant for the solvent extraction.

(2) A second embodiment of the present invention provides the method of recovering scandium according to the first embodiment, comprising: performing scrubbing, the scrubbing comprising: mixing a washing liquid with the extractant after the solvent extraction to separate scandium contained in the extractant into the washing liquid, the washing liquid comprising a sulfuric acid solution having a concentration between 1.0 mol/L or more and 3.0 mol/L or less; and recovering scandium from the washing liquid after the scrubbing.

(3) A third embodiment of the present invention provides the method of recovering scandium according to the first embodiment, comprising: adding a carbonate salt to the extractant after the solvent extraction to perform backward extraction, thereby obtaining a post-backward extraction extractant and a backward extraction liquid.

(4) A fourth embodiment of the present invention provides the method of recovering scandium according to the third embodiment, in which the post-backward extraction extractant is repeatedly used as the extractant for the solvent extraction.

(5) A fifth embodiment of the present invention provides the method of recovering scandium according to any one of the first to fourth embodiment, in which the scandium-containing solution to be subjected to the solvent extraction is a post-sulfuration liquid obtained by hydrometallurgy of nickel oxide ore, the hydrometallurgy comprising: a leaching step of leaching the nickel oxide ore with sulfuric acid under high temperature and high pressure to obtain a leachate; a neutralization step of adding a neutralizing agent to the leachate to obtain a neutralized precipitate containing impurities and a post-neutralization liquid; and a sulfuration step of adding a sulfurizing agent to the post-neutralization liquid to obtain nickel sulfide and a post-sulfuration liquid.

(6) A sixth embodiment of the present invention provides the method of recovering scandium according to any one of the first to fifth embodiments, comprising: adding a neutralizing agent to the eluent eluted from the ion exchange resin to adjust pH to the range of 5 to 6; performing solid-liquid separation to obtain a neutralized precipitate and a neutralized filtrate; and subjecting a re-dissolved liquid obtained by adding an acid to the neutralized precipitate to the solvent extraction.

(7) A seventh embodiment of the present invention provides the method of recovering scandium according to any one of the first to fifth embodiments, comprising: adding a neutralizing agent to the eluent eluted from the ion exchange resin to adjust pH to the range of 3.5 to 4.5; performing solid-liquid separation to obtain a primary neutralized precipitate and a primary neutralized filtrate; then further adding the neutralizing agent to the primary neutralized filtrate to adjust pH to the range of 5.5 to 6.5; performing solid-liquid separation to obtain a secondary neutralized precipitate and a secondary neutralized filtrate; subjecting a re-dissolved liquid obtained by adding an acid to the secondary neutralized precipitate to the solid-liquid separation.

(8) An eighth embodiment of the present invention provides the method of recovering scandium according to any one of the first to seventh embodiments, comprising: upon performing the oxalate-formation treatment of the raffinate liquid to obtain the precipitate of scandium oxalate, adjusting the pH of the raffinate liquid to the range between −0.5 or more and less than 1; adding the solution after the pH adjustment to an oxalic acid-containing solution to generate a precipitate of scandium oxalate.

Effects of the Invention

According to the present invention, high purity scandium can simply and efficiently be recovered from nickel oxide ore.

PREFERRED MODE FOR CARRYING OUT THE INVENTION

Below, specific embodiments of the method of recovering scandium according to the present invention (hereinafter referred to as the "present embodiments") will be described in more detail with reference to the drawings, but the present invention shall not be limited to these. The present invention can be implemented with appropriate modifications made without departing from the spirit of the present invention. Note that the phrase "X to Y" (X and Y may be any numerical values) as used herein means "X or more and Y or less".

<<1. Method of Recovering Scandium>>

Figure 1:
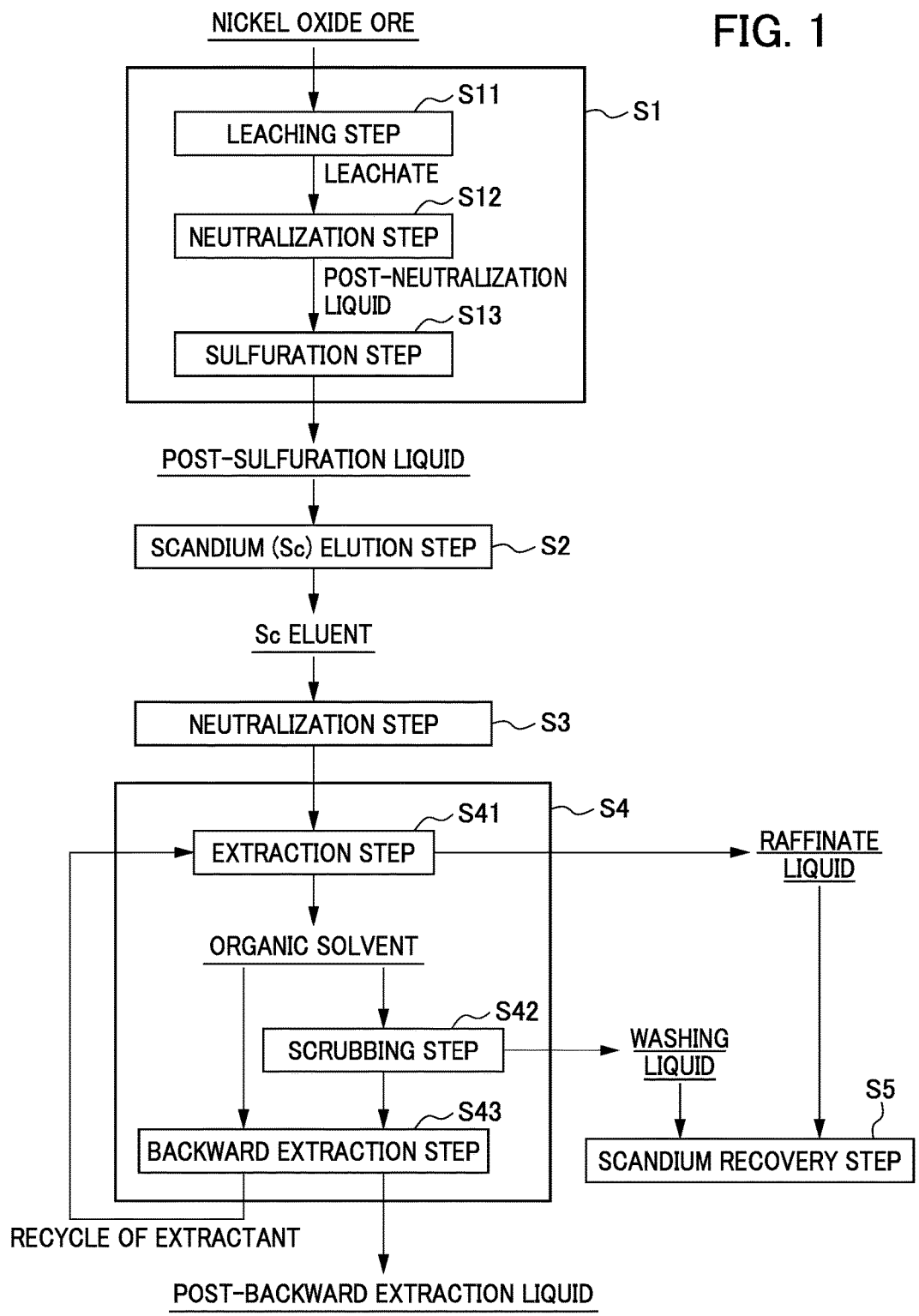
FIG. 1 shows a flow diagram for illustrating the method of recovering scandium.

FIG. 1 is a flow diagram showing an example of the method of recovering scandium according to the present embodiment. The above method of recovering scandium comprises: separating scandium from other impurities in a scandium-containing acidic solution obtained by leaching nickel oxide ore with an acid such as sulfuric acid, thereby simply and effectively recovering high purity scandium.

According to the above method of recovering scandium, the acidic scandium-containing solution is subjected to solvent extraction with amine-based extractant to extract impurities, in particular an actinoid element, thorium (Th), contained in the acidic solution into the extractant. This allows scandium to remain in the acidic solution after the solvent extraction, thereby achieving separation of scandium. Scandium remaining in the raffinate liquid after the solvent extraction is then subjected to a process of recovering scandium as a precipitate of an oxalate salt, the process involving performing oxalate-forming treatment using oxalic acid. This enables transformation of scandium into a solid form convenient as a product, and also enables separation of impurities such as residual uranium. As a result, scandium can be recovered as crystals of high purity scandium oxalate.

Note that the resulting crystals of scandium oxalate may be used as a material for electrolytes of fuel cells after transformed into scandium oxide by calcination according to a known method and the like, or may be added to aluminum to form an alloy after transformed into scandium metal by molten salt electrolysis and the like.

As described above, the present invention may be characterized by that solvent extraction treatment is performed using an amine-based solvent extraction agent when solvent extraction is performed to separate and recover scandium. According to such a method, even when a raw material such as nickel oxide ore which contains a large amount of impurities is used, impurities can be separated out more effectively, and stable operations can be performed, and high purity scandium can be recovered efficiently.

More specifically, as shown in the flow diagram of FIG. 1, the method of recovering scandium according to the present embodiment comprises: a hydrometallurgy treatment step S1 of leaching nickel oxide ore with an acid such as sulfuric acid to obtain a scandium-containing acidic solution; a scandium elution step S2 of removing impurities from the acidic solution to obtain a scandium eluate with scandium enriched; a solvent extraction step S4 of subjecting the scandium eluate to solvent extraction using an amine-based extractant to extract impurities into the extractant, allowing scandium to remain in the acidic solution after extraction, thereby achieving separation of scandium; and a scandium recovery step S5 of recovering scandium from the raffinate liquid. Alternatively, before the solvent extraction step S4, a neutralization step S3 may be performed, the neutralization step S3 comprising adding a neutralizing agent to the scandium eluate to perform neutralization treatment, thereby obtaining a solution (an extraction starting liquid) containing a high concentration of scandium.

<<2. Each Step of the Method of Recovering Scandium>>
<2-1. Step of Hydrometallurgy Treatment of Nickel Oxide Ore>

For the scandium-containing acidic solution from which scandium is to be recovered, an acidic solution obtained by treating nickel oxide ore with sulfuric acid can be used.

Specifically, for the acidic solution to be subjected to solvent extraction, a post-sulfuration liquid can be used which is obtained through the hydrometallurgy treatment step S1 of nickel oxide ore, the hydrometallurgy treatment step S1 comprising: a leaching step S11 of leaching nickel oxide ore with an acid such as sulfuric acid under high temperature and high pressure to obtain a leachate; a neutralization step S12 of adding a neutralizing agent to the leachate to obtain a neutralized precipitate containing impurities and a post-neutralization liquid; and a sulfuration step S13 of adding a sulfurizing agent to the post-neutralization liquid to obtain nickel sulfide and a post-sulfuration liquid. Below, the process flow of the hydrometallurgy treatment step S1 of nickel oxide ore will be described.

(1) Leaching Step

The leaching step S11 comprises adding sulfuric acid to a slurry of nickel oxide ore, for example, in a high temperature pressurized vessel (an autoclave) and the like, and stirred at a temperature of 240° C. to 260° C. to form a leach slurry comprising a leachate and a leach residue. Note that a treatment in the leaching step S11 can be performed according to the publicly known HPAL process, which is described, for example, in Patent Document 1.

Here, examples of nickel oxide ore include so-called laterite ore such as limonite ore and saprolite ore. The content of nickel in laterite ore is usually 0.8 to 2.5 wt %, and contained as a hydroxide or a silica magnesia (magnesium silicate) mineral. Further, these types of nickel oxide ore contain scandium.

In the leaching step S11, solid-liquid separation is performed to obtain a leachate containing nickel, cobalt, scandium, and the like; and a leach residue as a hematite while washing the resulting leach slurry comprising the leachate and the leach residue. In the above solid-liquid separation treatment, for example, the leach slurry is mixed with a washing liquid, and then solid-liquid separation is performed in a solid-liquid separation apparatus such as a thickener using an aggregating agent supplied from an apparatus for supplying an aggregating agent and the like. Specifically, the leach slurry is first diluted with the washing liquid, and then the leach residue in the slurry is condensed as a precipitate in the thickener. Note that in the above solid-liquid separation treatment, solid-liquid separation is preferably performed while washing the leach slurry by a multi-stage washing process using multistaged solid-liquid separation cells such as thickeners.

(2) Neutralization Step

The neutralization step S12 comprises adding a neutralizing agent to the leachate obtained from the aforementioned leaching step S11 to adjust pH, thereby obtaining a neutralized precipitate containing impurity elements and a post-neutralization liquid. After the neutralization treatment in the above neutralization step S12, valuable metals such as nickel, cobalt, and scandium will be contained in the post-neutralization liquid while most impurities including iron and aluminum will be included in the neutralized precipitate.

For the neutralizing agent, publicly known substances may be used, including, for example, calcium carbonate, slaked lime, sodium hydroxide, and the like.

In the neutralization treatment of the neutralization step S2, the pH is preferably adjusted to the range of 1 to 4, preferably to the range of 1.5 to 2.5 while preventing oxidation of the leachate separated. When the pH is less than 1, neutralization may be insufficient, and the neutralized precipitate and the post-neutralization liquid may not be separated. On the other hand, when the pH is more than 4, not only impurities including aluminum but also valuable metals such as scandium and nickel may be contained in the neutralized precipitate.

(3) Sulfuration Step

The sulfuration step S13 comprises adding a sulfurizing agent to the post-neutralization liquid obtained from the aforementioned neutralization step S12 to obtain nickel sulfide and a post-sulfuration liquid. Nickel, cobalt, zinc, and the like are transformed into sulfides, and scandium and the like is contained in the post-sulfuration liquid after the sulfuration treatment in the above sulfuration step S13.

Specifically, in the sulfuration step S13, a sulfurizing agent such as gaseous hydrogen sulfide, sodium sulfide and hydrogenated sodium sulfide is added to the resulting post-neutralization liquid to form sulfides (a mixture of nickel and cobalt sulfides) comprising nickel and cobalt with less impurity components; and a post-sulfuration liquid having a low and stabilized level of nickel and containing scandium and the like.

In the sulfuration treatment of the sulfuration step S13, sedimentation and separation treatment of a slurry of the mixture of nickel and cobalt sulfides is performed using a sedimentation apparatus such as a thickener to separate and recover the mixture of nickel and cobalt sulfides from the bottom of the thickener. Meanwhile, the post-sulfuration liquid as an aqueous solution component is overflown for recovery.

In the method of recovering scandium according to the present embodiment, the post-sulfuration liquid obtained through each step of the hydrometallurgy treatment step S1 of nickel oxide ore can be used as an acidic solution containing scandium and other impurities, the acidic solution being a target for the process for recovering scandium.

<2-2. Scandium (Sc) Elution Step>

As described above, the post-sulfuration liquid as a scandium-containing acidic solution obtained by leaching nickel oxide ore with sulfuric acid may be used as a target solution for the process for recovering scandium. However, for example, the post-sulfuration liquid as a scandium-containing acidic solution contains, in addition to scandium, aluminum, chromium and various other impurities remaining in the solution without being sulfurized after the aforementioned sulfuration treatment in the sulfuration step S1. In view of the above, a scandium eluate (scandium-containing solution) is preferably generated by preliminarily removing impurities contained in the acidic solution to enrich scandium (Sc) in the scandium elution step S2 before the acidic solution is subjected to solvent extraction.

In the scandium elution step S2, impurities such as aluminum contained in the acidic solution may be separated and removed by a method of ion exchange treatment, for example, using a chelating resin to obtain a scandium-containing solution with scandium enriched.

Figure 2:
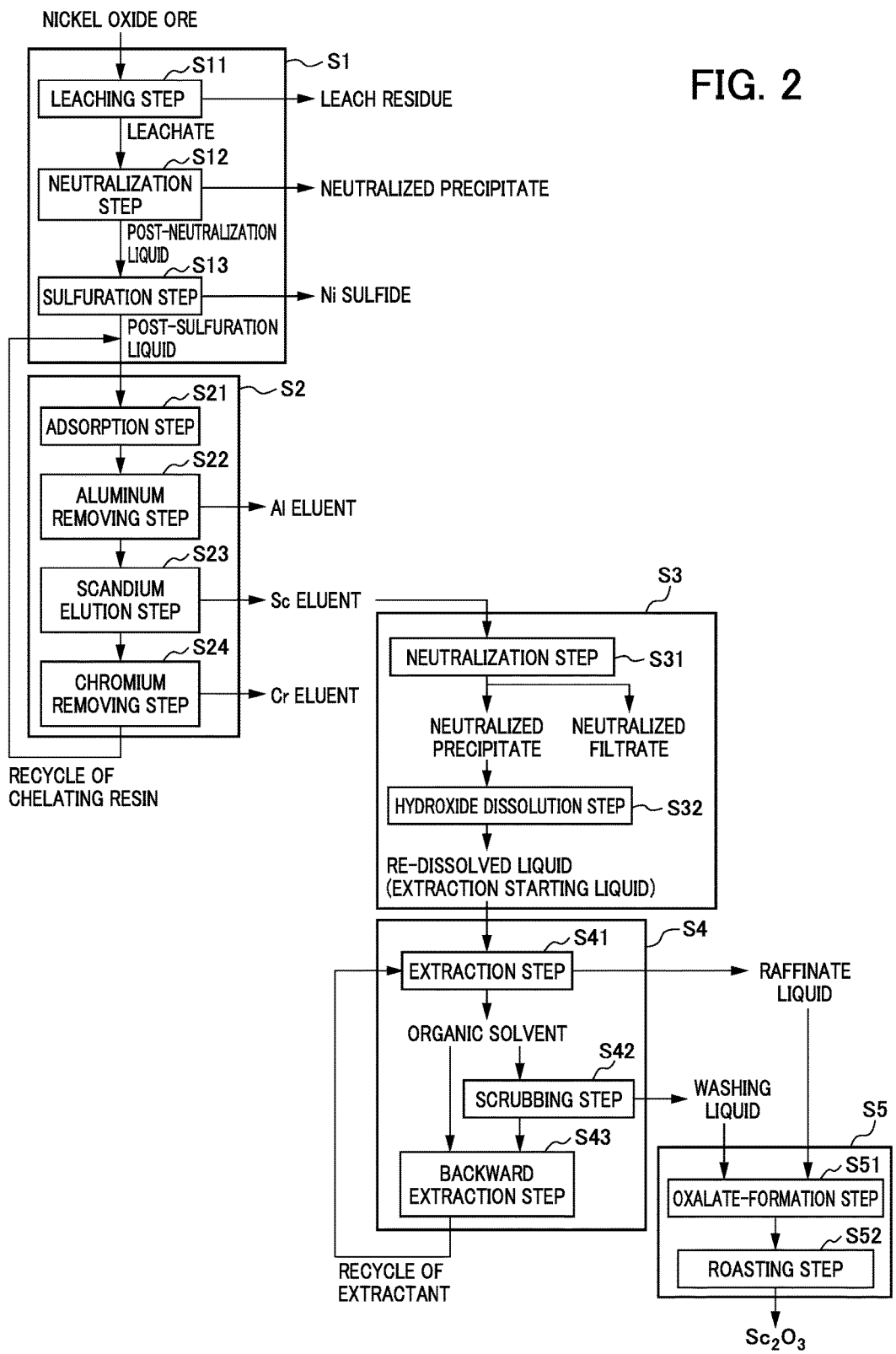
FIG. 2 shows a flow diagram for illustrating an example of the entire process flow in which the method of recovering scandium is used.

FIG. 2 represents a flow diagram showing an example of the method of removing impurities contained in the acidic solution to enrich and elute scandium, comprising a step (an ion exchange step) of performing an ion exchange reaction using a chelating resin. In this step, the post-sulfuration liquid obtained from the sulfuration step S13 in the hydrometallurgy treatment step S1 of nickel oxide ore is brought into contact with a chelating resin to allow scandium in the post-sulfuration liquid to be adsorbed by the chelating resin, and then a scandium (Sc) eluent is obtained. Note that the ion exchange step as an example of the scandium elution step S2 is referred to the "ion exchange step S2".

Specifically, examples of the ion exchange step S2 include a step comprising: an adsorption step S21 of bringing the post-sulfuration liquid into contact with a chelating resin to allow scandium to be adsorbed by the chelating resin; an aluminum removing step S22 of allowing 0.1 N or less of sulfuric acid to make contact with the chelating resin which has adsorbed scandium to remove aluminum adsorbed by the chelating resin; a scandium elution step S23 of allowing 0.3 N or more and 3 N or less of sulfuric acid to make contact with the chelating resin to obtain a scandium eluate; and a chromium removing step S24 of allowing 3 N or more of sulfuric acid to make contact with the chelating resin which has been subjected to the scandium elution step S23 to remove chromium which has been adsorbed by the chelating resin in the adsorption step S21. Below, an overview of each step will be described, but the ion exchange step S2 shall not be limited to it.

[Adsorption Step]

In the adsorption step S21, the post-sulfuration liquid is brought into contact with a chelating resin to allow scandium to be adsorbed by the chelating resin. There is no particular limitation for the type of the chelating resin, and for example, a resin having iminodiacetic acid as a functional group can be used.

[Aluminum Removing Step]

In the aluminum removing step S22, the chelating resin which has adsorbed scandium in the adsorption step S21 is brought into contact with 0.1 N or less of sulfuric acid to remove aluminum adsorbed by the chelating resin. Note that when removing aluminum, the pH is preferably maintained in the range of between 1 or more and 2.5 or less, and more preferably maintained in the range of between 1.5 or more and 2.0 or less.

[Scandium Elution Step]

In the scandium elution step S23, the chelating resin which has been subjected to the aluminum removing step S22 is brought into contact with 0.3 N or more and less than 3 N of sulfuric acid to obtain a scandium eluent. When obtaining the scandium eluent, the normality of sulfuric acid used as an eluent is preferably maintained in the range of between 0.3 N or more and less than 3 N, and more preferably maintained in the range of between 0.5 N or more and less than 2 N.

[Chromium Removing Step]

In the chromium removing step S24, the chelating resin which has been subjected to the scandium elution step S23 is brought into contact with 3 N or more of sulfuric acid to remove chromium which has been adsorbed by the chelating resin in the adsorption step S21. A normality of sulfuric acid used as an eluent of less than 3 N is not preferred when removing chromium because chromium may not be removed properly from the chelating resin.

<2-3. Neutralization Step>

As described above, in the scandium elution step S2, scandium is separated from impurities by virtue of the selectivity of the chelating resin, and scandium separated from impurities is recovered as a scandium eluate. However, all impurities may not be completely separated from scandium due to the limited capability of a chelating resin to be used. Further, actinoid elements such as thorium show the same behavior as scandium, and thus separation is difficult.

Accordingly, separation of scandium from impurities can be further facilitated by subjecting the scandium eluate collected in the scandium elution step S2 to solvent extraction using as the scandium eluate an extraction starting liquid in the solvent extraction step S4 described below.

However, in general, higher is the concentration of the target component in the extraction starting liquid to be subjected to solvent extraction, the higher is the separation performance of unwanted impurities in the solvent extraction step S4. Further, a less amount of a liquid will be subjected to solvent extraction when a higher concentration of scandium is contained in the extraction starting liquid, assuming the same amount of scandium is to be processed. As a result, a less amount of an extractant will be used. This can further provide various advantages such as improved operating efficiency owing to smaller equipment for the solvent extraction treatment.

In view of the above, in order to increase the concentration of scandium in the scandium eluate, i.e., in order to concentrate scandium, a neutralizing agent is added to the scandium eluate eluted from the chelating resin in the scandium elution step S2 (the scandium elution step S23) to adjust pH, thereby forming a precipitate of scandium hydroxide. The resulting precipitate of scandium hydroxide is then re-dissolved by adding an acid to obtain a highly concentrated scandium solution (an extraction starting liquid). As described above, the process efficiency of solvent extraction can be improved by subjecting the scandium eluate to the neutralization treatment before the solvent extraction step S4 to concentrate scandium.

Moreover, un-precipitated impurities may be separated out by subjecting a scandium-containing precipitate to solid-liquid separation, the scandium-containing precipitate being temporarily formed from the scandium eluate after performing the aforementioned neutralization treatment.

Specifically, as shown in FIG. 2, the above neutralization step S3 comprises a neutralization step S31 of adding a neutralizing agent to the scandium eluate to adjust the pH to a predetermined pH range to obtain a neutralized residue and a neutralized filtrate; and a hydroxide dissolution step S32 of dissolving the resulting neutralized precipitate by adding an acid to obtain a re-dissolved liquid containing a high concentration of scandium.

[Neutralization Step]

In the neutralization step S31, a neutralizing agent is added to the scandium eluate to adjust the pH of the solution to the range of 5 to 6, transforming scandium contained in the scandium eluate into a precipitate of scandium hydroxide. A neutralized precipitate comprising scandium hydroxide and a neutralized filtrate are generated as described above in the neutralization step S31.

There is no particular limitation for the neutralizing agent, and for example, sodium hydroxide and the like may be used.

Moreover, the pH adjustment by neutralization with a neutralizing agent in the neutralization step S31 may be performed in two steps, enabling more efficient separation of impurities.

Specifically, in the neutralization treatment by pH adjustments in two steps, a neutralizing agent such as sodium hydroxide is first added to the scandium eluate to perform the first stage of neutralization so that the pH of the solution is adjusted to the range of 3.5 to 4.5, preferably to around pH 4. In this first stage of neutralization, most of impurities such as iron and chromium which are less basic than scandium are transformed into a precipitate in the form of hydroxides, and a primary neutralized precipitate are separated from a primary neutralized filtrate by filtration.

Next, the second stage of neutralization is performed in which a neutralizing agent such as sodium hydroxide is further added to the primary neutralized filtrate obtained from the first stage of neutralization so that the pH of the filtrate is adjusted to the range of 5.5 to 6.5, preferably to around pH 6. In the above second stage of neutralization, scandium hydroxide can be obtained as a secondary neutralized precipitate while nickel, which is more basic than scandium, does not precipitate and thus remains in a secondary neutralized filtrate. Therefore, the secondary neutralized precipitate, i.e., a hydroxide of scandium from which impurities have been separated out can be obtained by performing solid-liquid separation.

The concentration of sodium hydroxide and the like used as a neutralizing agent in the neutralization treatment may be appropriately selected. However, local increase in pH may occur in a reaction vessel when a highly concentrated neutralizing agent of more than 4 N is added. This may result in a local pH of more than 4.5. If this occurs, impurities may disadvantageously be co-precipitated with scandium, and thus high purity scandium may not be obtained. For this reason, a neutralizing agent is preferably a solution diluted to 4 N or less so that neutralization in a reaction vessel proceeds as uniformly as possible.

On the other hand, when the concentration of a neutralizing agent such as a sodium hydroxide solution is too low, the amount of the solution to be added increases accordingly. This is not preferred because the amount of liquid to be handled increases, resulting in a larger equipment size and thus increased cost. For this reason, a neutralizing agent with a concentration of more than 1 N is preferably used.

Note that a precipitate obtained by adding an alkaline neutralizing agent such as sodium hydroxide, like the aforementioned primary neutralized precipitate and secondary neutralized precipitate, usually has very poor filterability. Therefore, a seed crystal may be added to improve filterability when performing neutralization. A seed crystal is preferably added in an amount of about 1 g/l or more relative to a solution before the neutralization treatment.

[Hydroxide Dissolution Step]

In the hydroxide dissolution step S32, the neutralized precipitate mainly comprising scandium hydroxide recovered through the aforementioned one-step or two-step neutralization treatment in the neutralization step S31 is re-dissolved by adding an acid to obtain a re-dissolved liquid. In the present embodiment, the re-dissolved liquid obtained as described above is preferably subjected to the solvent extraction treatment described below using the re-dissolved liquid as an extraction starting liquid.

There is no particular limitation the acid for dissolving the neutralized precipitate, but sulfuric acid is preferably used. Note that the re-dissolved liquid is a scandium sulfate solution when sulfuric acid is used.

For example, when sulfuric acid is used, there is no particular limitation for the concentration thereof, but a sulfuric acid solution with a concentration of 2 N or more is preferably used for dissolution in view of the industrially preferred rate of reaction.

Note that an extraction starting liquid with any concentration of scandium can be obtained by adjusting the concentration of slurry when performing dissolution with sulfuric acid and the like. For example, when 2 N sulfuric acid is added to perform dissolution, the pH of the solution is preferably maintained at pH 1. Scandium hydroxide can be efficiently dissolved, and the loss in the recovery of scandium due to undissolution can be reduced when dissolution is performed while maintaining the pH to this value.

<2-4. Solvent Extraction Step>

Next, in the solvent extraction step S4, the scandium-containing solution (the scandium eluate) obtained from the scandium elution step S2 or the re-dissolved liquid obtained through the neutralization step S3 of subjecting the scandium solution to the neutralization treatment is allowed to make contact with an extractant to obtain a raffinate liquid which contains scandium. Note that the scandium eluate and re-dissolved liquid to be subject to solvent extraction are acidic solutions containing scandium and other impurity elements as described above. These are each referred to as a "scandium-containing solution".

There is no particular limitation for the aspect of the solvent extraction step S4, but a solvent extraction, for example, as shown in FIGS. 1 and 2, is preferably performed, the solvent extraction comprising: an extraction step S41 of mixing the scandium-containing solution with an organic solvent as an extracting agent to allow separation of a post-extraction organic solvent into which impurities and a trace amount of scandium are extracted and a raffinate liquid in which scandium remains; a scrubbing step S42 of mixing the post-extraction organic solvent with a sulfuric acid solution to separate a trace amount of scandium extracted into the post-extraction organic solvent into an aqueous phase, thereby obtaining a post-washing liquid; and a backward extraction step S43 of adding a backward extracting agent to the post-washing organic solvent to perform backward extraction of impurities from the post-washing organic solvent.

(1) Extraction Step

In the extraction step S41, a scandium-containing solution is mixed with an organic solvent containing an extracting agent to selectively extract impurities, in particular thorium (Th) into the organic solvent, thereby obtaining an organic solvent containing impurities and a raffinate liquid. The method of recovering scandium according to the present embodiment can be characterized by that solvent extraction treatment is performed using an amine-based extractant in the extraction step S41. Impurities such as thorium can be extracted more efficiently and effectively to separate scandium by performing solvent extraction treatment using an amine-based extractant.

Here, the amine-based extractant has a low selectively for scandium, and does not require a neutralizing agent during extraction, and may have other characteristics. For example, the followings can be used as the amine-based extractant: those known under the trade names of, for example, a primary amine PRIMENE JM-T, a secondary amine LA-1, a tertiary amine TNOA (Tri-n-octylamine), TIOA (Tri-i-octylamine), and the like.

When performing extraction, the amine-based extractant is preferably used after diluted with, for example, a hydrocarbon-based organic solvent and the like. There is no particular limitation for the concentration of the amine-based extractant in an organic solvent, but it is preferably about 1 vol % or more and about 10 vol % or less, in particular more preferably about 5 vol %, in view of phase separability during the extraction and backward extraction described below.

Moreover, there is no particular limitation for the volume ratio of the organic solvent and the scandium-containing solution when performing extraction, but the molar amount of the organic solvent is preferably 0.01 times or more and 0.1 times or less relative to the molar amount of metal in the scandium-containing solution.

(2) Scrubbing (Washing) Step

When a trace amount of scandium is co-existent in a solvent into which impurities are extracted from the scandium-containing solution in the extraction step S41 as described above, a scrubbing (washing) treatment (the scrubbing step S42) is performed on the organic solvent (the organic phase) to separate scandium into the aqueous phase, thereby recovering scandium from the extractant before performing backward extraction of the extract liquid obtained from the extraction step S41.

Washing the organic solvent to separate a trace amount of scandium extracted with the extractant in the scrubbing step S42 as described above can allow scandium to separate into a washing liquid, and thus can further improve the recovery rate of scandium.

For a solution (a washing solution) used for scrubbing, a sulfuric acid solution, a hydrochloric acid solution, and the like can be used. Further, solutions to which water-soluble chlorides and sulfates are added can also be used. Specifically, when a sulfuric acid solution is used as a washing solution, a solution having a concentration in the range of between 1.0 mol/L or more and 3.0 mol/L or less is preferably used.

The number of washing stages (the number of times) may also depend on the identities and concentrations of impurity elements, and thus may appropriately be selected depending on the amine-based extractant, extraction conditions, and the like to be used. For example, when the phase ratio of the organic phase (O) to the aqueous phase (A), O/A is 1, the number of washing stages of about 3 to 5 can allow scandium extracted into the organic solvent to be separated below the detection limit of an analyzer.

(3) Backward Extraction Step

In the backward extraction step S43, impurities are backward-extracted from the organic solvent used for extracting impurities in the extraction step S41. Specifically, in the backward extraction step S43, the backward extraction solution (the backward extraction starting liquid) is added to and mixed with an organic solvent containing an extractant to effect a reaction opposite to that in the extraction treatment of the extraction step S41. This enables backward extraction of impurities to give a post-backward extraction liquid containing impurities.

As described above, impurities are selectively extracted using an amine-based extractant in the extraction treatment of the extraction step S41. Therefore, a solution containing a carbonate salt such as sodium carbonate and potassium carbonate is preferably used as the backward extraction solution in view of effective separation of these impurities from the organic solvent containing an extractant to regenerate the extractant.

For example, the concentration of a carbonate-containing solution serving as the backward extraction solution is preferably about 0.5 mol/L or more and 2 mol/L or less in view of avoidance of excessive use.

Note that when scrubbing treatment is performed for the organic solvent containing an extractant in the scrubbing step S42 as described above, a backward extraction solution may similarly be added to the post-scrubbing extractant to perform the backward extraction treatment.

An extractant from which impurities has been separated out by performing the backward extraction treatment in which a solution of a carbonate salt such as sodium carbonate is added to a post-extraction extractant or a post-scrubbing extractant as described above can be used again repeatedly as an extractant in the extraction step S41.

<2-5. Scandium Recovery Step>

Next, in the scandium recovery step S5, scandium is recovered from the raffinate liquid obtained from the extraction step S41 in the solvent extraction step S4, or from the washing liquid after scrubbing when scrubbing is performed in the scrubbing step S42.

There is no particular limitation for the method of recovering scandium, and any known method can be used. However, for example, a method of recovering scandium as a precipitate of an oxalate salt using an oxalic acid solution (the oxalate-formation treatment) is more preferred than a method of recovering scandium as a precipitate of scandium hydroxide by performing neutralization with an alkaline substance. This is because impurities can be separated even more effectively.

In the method of recovering scandium via the oxalate-formation treatment, oxalic acid is added to the raffinate liquid and the washing liquid to form a precipitate of scandium oxalate, and then scandium oxalate is dried and roasted to recover scandium as scandium oxide. Below, a method of recovering scandium as scandium oxide, comprising performing roasting treatment after the oxalate formation will be described more specifically with referring to the flow diagram shown in FIG. 2.

[Oxalate-Formation Step]

In the oxalate-formation step S51, the raffinate liquid and the washing liquid obtained from the solvent extraction step S4 are mixed with a predetermined amount of oxalic acid to form a solid precipitate of scandium oxalate, which is then separated.

There is no particular limitation for the amount of oxalic acid to be added, but it is preferably 1.05 times or more and 1.2 times or less relative to the equivalent amount required to precipitate scandium contained in the raffinate liquid and the like as an oxalate salt. Note that the amount of oxalic acid $((COOH)_2)$ required to precipitate scandium (Sc) as scandium oxalate $(Sc_2(C_2O_4))$ is defined as 1 equivalence.

An addition amount of less than 1.05 times of the required equivalent amount is not preferred because the total recovery of scandium may not be achieved. On the other hand, when the addition amount is more than 1.2 times of the equivalent amount required for precipitation, the solubility of scandium oxalate is increased, and thus scandium may be re-dissolved, resulting in a decreased recovery rate, or the amount of an oxidizing agent such as sodium hypochlorite, which is used for decomposing excess oxalic acid, may be increased.

Specifically, in the above oxalate-formation step S51, sulfuric acid or the like is added to a scandium-containing solution such as the raffinate liquid to obtain a scandium-containing solution in which the pH of the solution is adjusted to the range of between −0.5 or more and less than 1. Subsequently, the scandium-containing solution after this pH adjustment is mixed with an oxalic acid solution to obtain crystals of scandium oxalate.

When the pH of the solution is more than 1 in the pH adjustment with sulfuric acid or the like, precipitates of impurities such as divalent iron ions and aluminum ions contained in the solution may be formed. On the other hand, when the pH is in an extremely strong acidic region of less than −0.5 (negative 0.5), the solubility of precipitating scandium oxalate is increased, and the amount of crystals obtained may be decreased, resulting in a reduced yield.

Here, in the above oxalate-formation treatment, uranium in particular among the aforementioned impurities does not precipitate and remains in the raffinate liquid, and thus can be completely separated from scandium. However, some of iron may also precipitate, affecting the grade of scandium oxalate.

Accordingly, when the scandium-containing solution after the pH adjustment is mixed with an oxalic acid solution in the oxalate-formation treatment, not only the conventionally performed method but also the so-called reversed addition method can be used to obtain crystals of scandium oxalate. In the conventionally performed method, an oxalic acid solution is added to a reaction vessel filled with the treatment target solution, i.e., the scandium-containing solution after the pH adjustment. In the so-called reversed addition method, the scandium-containing solution after the pH adjustment is added to a large amount of an oxalic acid solution contained in a reaction vessel.

Co-precipitation of iron with scandium oxalate can effectively be prevented by forming crystals of scandium oxalate according to the reversed addition method as described above. This can be achieved without performing oxidation treatment of adding an oxidizing agent in advance even when the concentration of iron remaining in the scandium-containing liquid after the pH adjustment is high.

Note that the crystals of scandium oxalate obtained from the above oxalate-formation treatment may be washed after performing solid-liquid separation, and subjected to the roasting step S53 described below to obtain high purity scandium oxalate.

[Roasting Step]

In the roasting step S52, the precipitate of scandium oxalate obtained from the oxalate-formation step S51 is washed with water, and dried, and then roasted. Scandium can be recovered as ultra high purity scandium oxide via the roast treatment.

There is no particular limitation for the roasting conditions, but for example, heating in a tubular furnace at about 900° C. for about 2 hours may be used. Note that a continuous furnace such as a rotary kiln is preferably used for industrial production because both drying and roasting can be performed with the same equipment.

EXAMPLES

Below, the present invention will be described in more detail with reference to Examples. However, the present invention shall not in any sense be limited to these Examples.

Example 1

[Preparation of Scandium-Containing Solution (Pre-Extraction Liquid)]

Pressurized acid leaching of nickel oxide ore with sulfuric acid was performed according to the known method such as the method described in Patent Document 1. The pH of the resulting leachate was adjusted to remove impurities, and then a sulfurizing agent was added to remove nickel, thereby preparing a post-sulfuration liquid. Note that the main compositions of the post-sulfuration liquid are shown in Table 1 below.

Note that when a neutralizing agent was added to a solution having the above composition to form a precipitate, thereby obtaining a hydroxide comprising scandium and other impurity components, the grade of scandium hydroxide was as low as about 0.1 wt %.

TABLE 1

| Composition of post-sulfuration liquid | Sc | Al | Fe |
|---|---|---|---|
| [mg/L] | 14 | 2,800 | 1,000 |

Next, in view of testing separation and purification effects, reagents were added as impurities, if needed, to the post-sulfuration liquid obtained in order to target elemental components which were not contained in the original nickel oxide ore. The solution was then subjected to ion exchange treatment by the known method using a chelating resin. Enrichment treatment was further performed by means of heating and the like to obtain a pre-extraction liquid having the composition shown in Table 2 below. The composition of the pre-extraction liquid is shown in Table 2.

The term "Others" in the component list of Table 2 and the tables hereafter collectively refers to various elements such as elements contained in nickel oxide ore such as nickel, magnesium, chromium, manganese, calcium, and cobalt; elements from the neutralizing agent added when treating nickel oxide ore; and elements introduced as reagents in the present Examples which are otherwise not usually present or which are present only in trace amounts. "Others" is expressed as the total analytical values of these components that were able to be detected. Note that aluminum and iron are not included in "Others" in the present Examples.

Note that when a neutralizing agent is added to the eluent concentrated to the composition shown in Table 2 below, and scandium and other impurity components were precipitated as a hydroxide, scandium hydroxide having a grade of about 50 wt % was obtained. This was not suitable for uses requiring a high purity.

TABLE 2

| Composition of pre-extraction liquid | Sc | Al | Fe | Th | Others |
|---|---|---|---|---|---|
| [mg/L] | 20,000 | 11,000 | 4,200 | 220 | 1,900 |

[Solvent Extraction]
[Extraction Step]

Next, 50 liters of an organic solvent in which an amine-based extractant (The Dow Chemical Company, PRIMENE JM-T) was adjusted to 5 vol % with a solvent (SHELLSOL A150, Shell Chemicals Japan, Ltd.) was added to 100 liters of a solution having the composition shown in Table 2 as an extraction starting liquid, and stirred at room temperature for 60 minutes to effect solvent extraction treatment, thereby obtaining a raffinate liquid containing scandium. Note that no clading was formed during extraction, and phase separation after allowed to stand also proceeded rapidly.

The content of each element contained in the organic phase extract obtained by the above extraction was analyzed. An extraction rate (%) was calculated by dividing the amount of each element contained in the organic phase extract by the amount of that element contained in the pre-extraction liquid. The results are shown in Table 3 below.

TABLE 3

| Extraction rates of various elements | Sc | Al | Fe | Th | Others |
|---|---|---|---|---|---|
| [%] | 4 | — | — | 85 | 23 |

As seen from the results of extraction rates in Table 3, the majority of scandium (Sc) contained in the pre-extraction liquid was partitioned into the raffinate liquid after the extraction step. Although Al, Fe, and the like were not extracted, other impurities were able to be separated. Further, thorium (Th) contained in the extraction starting liquid was extracted with a high extraction rate, and was able to be separated from scandium.

Note that even when a neutralizing agent was added to the resulting raffinate liquid to recover a precipitate containing a hydroxide of scandium, the grade of scandium hydroxide itself was 49 wt % to 50 wt %, showing little improvement largely due to the presence of large amounts of unseparated aluminum and iron.

[Scrubbing (Washing) Step]

Subsequently, 50 liters of a 1 mol/L sulfuric acid solution was mixed with 50 liters of the organic solvent containing scandium obtained from the extraction step (the organic phase extract) so that the phase ratio (O/A) became 1, and stirred for 60 min., and then washed. Then, it was allowed to stand for separation of the aqueous phase. The organic phase was again mixed with 50 liters of a fresh 1 mol/L sulfuric acid solution, and washed. The aqueous phase was then separated in a similar manner. The washing operation as described above was repeated 5 times in total.

By washing the organic phase extract for 5 times, scandium contained in the organic phase extract was allowed to separate into the aqueous phase, enabling recovery of scandium. In contrast, impurities contained in the organic phase extract were eluted at levels of as low as 1 mg/L, showing that only scandium extracted into the organic solvent was able to be effectively separated into the aqueous phase, and only impurities were able to be removed.

[Backward Extraction Step]

Subsequently, 1 mol/L sodium carbonate was mixed with the organic phase extract after washing so as to give a phase ratio O/A of 1/1, and stirred for 60 minutes to effect backward extraction of impurities into the aqueous phase.

The composition of various elements contained in the post backward extraction liquid obtained by the above backward extraction operations was analyzed. A recovery rate (%) was calculated by dividing the amount of each element contained in the post-backward extraction liquid by the amount of that element extracted into the organic phase in the extraction step. The results are shown in Table 4 below.

TABLE 4

| Recovery rates of various elements | Sc | Al | Fe | Th | Others |
|---|---|---|---|---|---|
| [%] | 25 | — | — | 100 | >99 |

As seen from the results of recovery rates in Table 4, all of thorium and most of other impurities contained in the pre-extraction liquid were able to be separated into the extractant, and most of scandium (Sc) recoverable from the raffinate liquid and the post-washing liquid was able to be recovered by performing the solvent extraction treatment as described above.

[Oxalate-Formation Step S7]

Next, crystals of oxalic acid dihydrate (Mitsubishi Gas Chemical Company, Inc.) was dissolved in the resulting raffinate liquid in an amount calculated to be twice of the amount of scandium contained in that raffinate liquid, and stirred and mixed for 60 minutes to generate a white crystalline precipitate of scandium oxalate.

[Roasting Step S8]

Next, the resulting precipitate of scandium oxalate was filtered by aspiration, and washed with pure water, and was dried at 105° C. for 8 hours. Then, the dried scandium oxalate was placed in a tubular furnace, and maintained at 850 to 900° C. to perform roasting (calcination), thereby obtaining scandium oxide.

The resulting scandium oxide obtained by performing roasting was analyzed by the emission spectroscopic analysis. Table 5 below shows the removal rates (%) each obtained by dividing the content of a material after roasting by the content of that material before the oxalate-formation step.

TABLE 5

| Removal rates of various elements | Sc | Al | Fe | Others |
|---|---|---|---|---|
| [%] | 0 | 100 | 99.9 | 99 |

As seen from the results of the removal rates in Table 5, aluminum, iron, and other impurities other than scandium were able be removed almost completely, and ultra high purity scandium oxide in which the purity as scandium oxide ($Sc_2O_3$) was more than 99.9 wt % was able to be obtained.

Comparative Example 1

The same ore as used in Example 1 was leached with sulfuric acid. The resulting leachate was subjected to neutralization treatment, and then passed through an ion exchange resin to obtain a pre-extraction liquid having a composition shown in Table 2 above. This solution was not subjected to the solvent extraction step, but was directly treated according to the oxalate-formation step. Except these, the same method was used as in Example 1.

As a result, aluminum and iron were almost completely separated out, but other impurity components, in particular thorium, were not able to be separated. The purity as scandium oxide ($Sc_2O_3$) after roasting was 99.2 wt %, which was lower than the purity obtained by the method according to Example 1 in which the solvent extraction treatment and the oxalate-formation treatment were combined.

Example 2

The post-sulfuration liquid having the composition shown in Table 1 above used in Example 1 was subjected to ion exchange treatment according to the same approach as used in Example 1. Then, the resulting scandium eluate was subjected to neutralization treatment in which sodium hydroxide was added to adjust pH to 6, thereby obtaining a neutralized precipitate. Subsequently, sulfuric acid was added to the resulting neutralized precipitate (scandium hydroxide) for re-dissolution, and reagents and the like were added as in Example 1, if needed, to obtain a chelate eluent (a hydroxide solution) having a composition shown in Table 6 below, which was taken as a pre-solvent extraction liquid.

TABLE 6

| Composition of pre-extraction liquid | Sc | Al | Fe | Th |
|---|---|---|---|---|
| [mg/L] | 22,000 | 3,500 | 1,000 | 26 |

The chelate eluent (the hydroxide eluent) having the composition shown in Table 6 as an extraction starting liquid was subjected to solvent extraction with an amine-based extractant.

Note that the amine-based extractant was prepared by diluting PRIMENE JM-T (The Dow Chemical Company) to 5 vol % with a solvent (SHELLSOL A150, Shell Chemicals Japan, Ltd.) as in Example 1. An extraction equilibrium pH of 1 was selected, and the amount of organic matter (O) and the amount of an extraction starting liquid (A) were selected as shown in Table 7 below based on the amount of organic matter and the amount of metal in the liquid.

TABLE 7

| (Extraction conditions) | Amount of organic liquid [ml] | Amount of aqueous-phase liquid [ml] | Organic matter/metal [mol/mol] | O/A |
|---|---|---|---|---|
| Example 2-1 | 100 | 200 | 0.02 | 0.5 |
| Example 2-2 | 150 | 200 | 0.03 | 0.75 |
| Example 2-3 | 200 | 200 | 0.04 | 1 |

Figure 3:
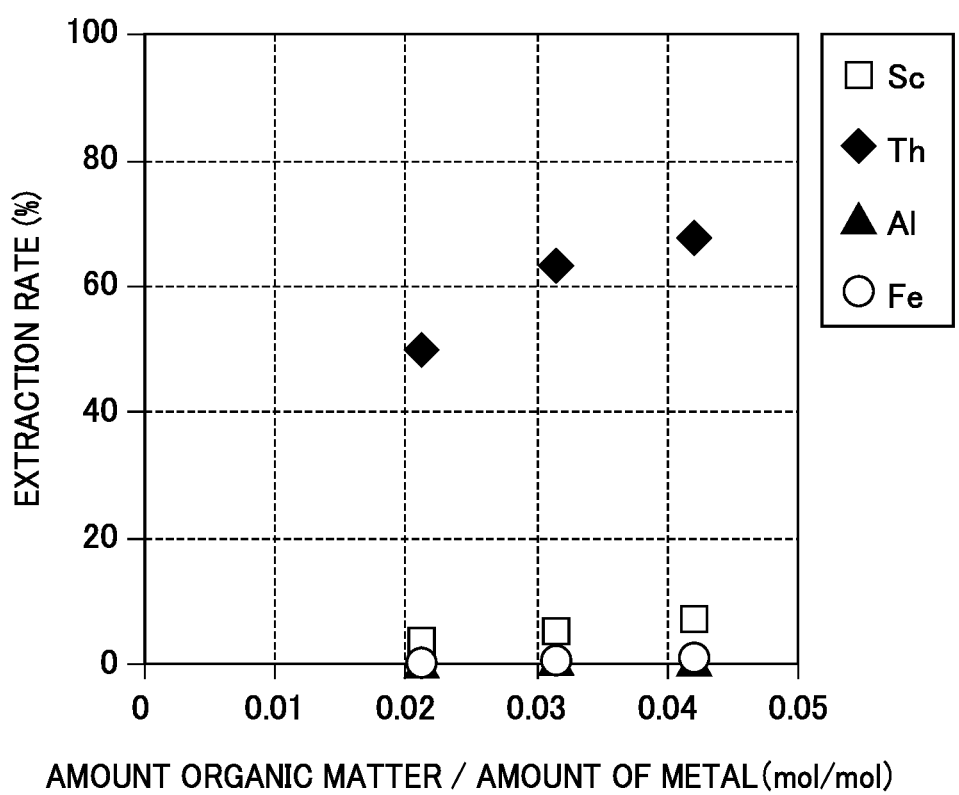
FIG. 3 is a graphic representation showing the extraction rates of Sc, Al, Th, and Fe which are contained in an organic solvent after solvent extraction treatment according to Examples.

FIG. 3 is a graphical representation showing the results of the extraction rates (%) of Sc, Al, Fe, and Th which were contained in the organic solvent after solvent extraction. Note that the extraction rates were expressed as percentages each calculated by dividing the amount of each element contained in the organic phase extract by the amount of that element contained in the pre-extraction liquid.

The graphical representation of FIG. 3 revealed that when the ratio of the amount of organic matter to the amount of metal, i.e., the amount of organic matter/the amount of metal (unit: mol/mol, the same hereinafter) is in the range of between 0.01 or more and 0.1 or less, scandium can be efficiently separated from thorium by the solvent extraction with an amine-based extractant, and thus scandium can be enriched in the raffinate liquid. Specifically, when O/A is 0.5 (the amount of organic matter/the amount of metal=0.02), the extraction rate of impurity thorium is 50%, and the extraction rate of scandium is 4%.

Note that the amount of organic matter/the amount of metal of less than 0.01 times is not preferred because the phase separation between the organic phase and the aqueous phase becomes poor. Moreover, the amount of organic matter/the amount of metal of more then 0.1 times is not preferred because more scandium will be contained in the organic phase.

Subsequently, the organic solvent obtained after extracting scandium according to Examples 2 to 3 was mixed with sulfuric acid, and subjected to washing treatment. Note that the concentrations of sulfuric acid used for washing are shown in Table 8.

TABLE 8

|  | Concentration of sulfuric acid [mol/L] |
|---|---|
| Example 2-3-1 | 1 |
| Example 2-3-2 | 3 |
| Example 2-3-3 | 4 |
| Example 2-3-4 | 5 |
| Example 2-3-5 | 6 |
| Example 2-3-6 | 7 |
| Example 2-3-7 | 8 |

Figure 4:
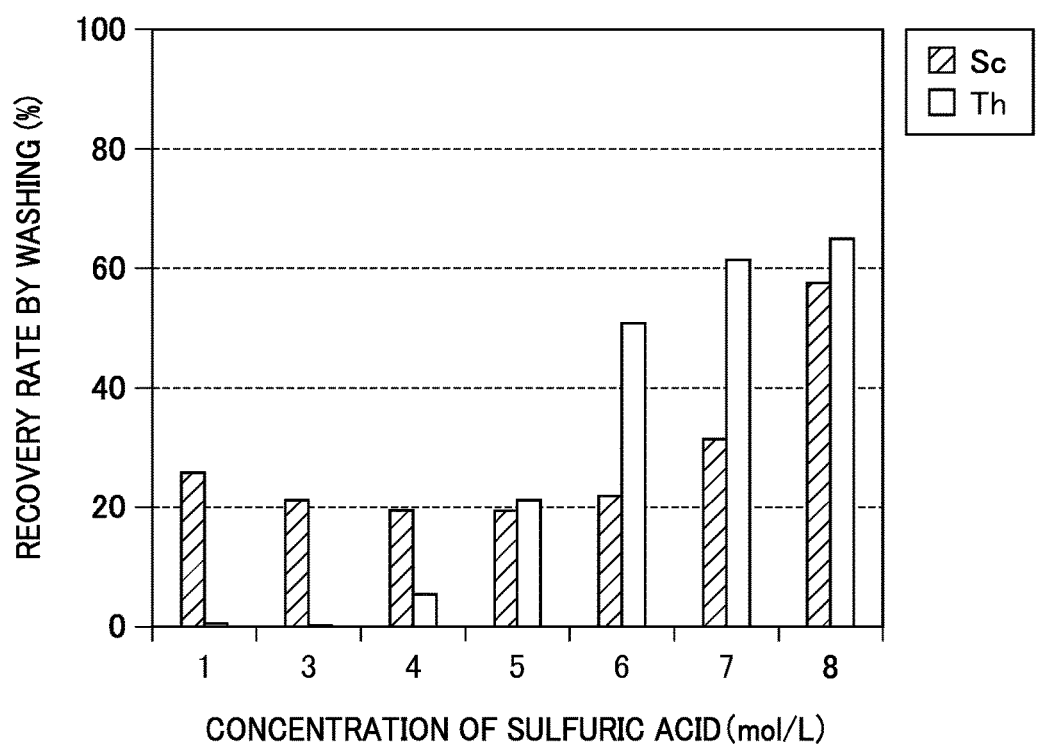
FIG. 4 is a graphic representation showing the relation between the concentration of sulfuric acid when the scrubbing (washing) treatment is performed by adding a sulfuric acid solution as a washing liquid to the extractant after the solvent extraction, and the washing rates (the recovery rates after washing) of scandium (Sc) and thorium (Th) according to Examples.

FIG. 4 is a graphical representation showing the relationship between the concentration of sulfuric acid used for washing and the washing rates of scandium and of thorium. Here, the washing rate refers to the rate of a metal which has been transferred to sulfuric acid from the organic solvent.

As seen in the graphical representation of FIG. 4, scandium was able to be separated and recovered from the organic solvent at any of the concentrations of sulfuric acid. In particular, when the concentration of sulfuric acid was 1 mol/L or more and 3 mol/L or less, only scandium was able to be efficiently separated and recovered from the organic solvent, leaving thorium behind in the organic solvent.

Example 3

Various impurities were added as reagents, if needed, as in Example 1 to the post-sulfuration liquid having the composition shown in Table 1 above as used in Example 1, and ion exchange treatment with a chelating resin was further performed according to the same approach, and sulfuric acid was passed through the chelating resin after the ion exchange treatment to obtain a scandium eluate having a composition shown in Table 9 below.

TABLE 9

| Scandium eluate | Sc | Al | Fe | Ni | Cr |
|---|---|---|---|---|---|
| [%] | 100 | 30 | 40 | 10 | 2 |

The resulting scandium eluate was placed in a container, and a 4 N sodium hydroxide solution was then added with stirring to adjust pH to 1. Subsequently, it was allowed to stand after stopping stirring. The amount of the liquid was then measured, and the supernatant after the precipitate was sedimented was collected. Then, stirring was re-started, and a 4 N sodium hydroxide solution was added again to adjust the pH of the solution to 2. Then it was allowed to stand after stopping stirring. The amount of the liquid was then measured, and the supernatant was collected. Then stirring was started again. This procedure was repeated to prepare samples of scandium eluates having a pH in the range of 1 to 6.

Each sample prepared was analyzed by ICP for the components shown in Table 9. Note that the amount calculated from the analytical value of each component and the fluid volume of each sample corresponds to the amount of that component present in the solution at each pH. The difference between the amount of the component present in the solution and the initial amount computed from the analytical value as shown in Table 9 and the initial volume of the scandium eluate corresponds to the amount of the precipitate generated by the pH adjustment (neutralization). The ratio obtained by dividing the amount of the precipitate by the aforementioned initial amount is defined as the precipitation rate (%).

Figure 5:
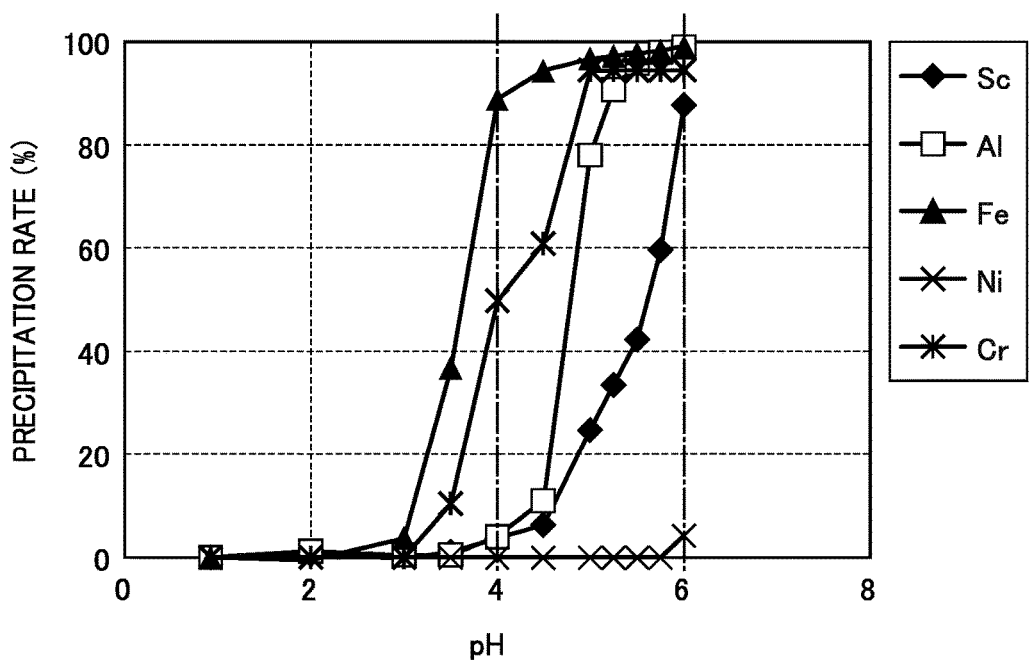
FIG. 5 is a graphical representation showing the pHs of the solutions when a neutralizing agent is added to the eluent eluted from chelating resin and the rate of each element precipitated from the solution (the precipitation rate).

FIG. 5 shows each pH and the precipitation rates of the component shown in Table 9. As shown in the graphical representation of FIG. 5, iron is found to show increased precipitation rates in the pH region of more than 3, and almost completely precipitated at 4.5 to 5 or more. Moreover, aluminum is found to show increased precipitation rates when the pH is 4.5 or more. In contrast, scandium is also found to show increased precipitation rates when the pH is more than 4.5, but the increase is more gradual than that of aluminum. Note that nickel starts to precipitate when the pH is becoming more than 6.

Based on the results shown in FIG. 5, a 4 N sodium hydroxide solution was added to a scandium eluate having a composition shown in Table 9 so that the pH of the solution was adjusted to 5 to 6, thereby achieving neutralization and forming a precipitate. Then, solid-liquid separation was performed to obtain a precipitate of scandium hydroxide.

Next, 2 N sulfuric acid was added to the resulting scandium hydroxide, and dissolution was performed while maintaining the pH at around 1 to obtain a re-dissolved liquid having a composition shown in Table 10 below.

TABLE 10

| Composition of pre-extraction liquid | Sc | Al | Fe |
|---|---|---|---|
| [g/L] | 20 | 10 | 4 |

Next, the resulting re-dissolved liquid as an extraction starting liquid was subjected to solvent extraction as in Example 1, and scandium oxalate was formed from the resulting raffinate liquid, and roasting was then performed to obtain scandium oxide. As a result, scandium oxide in which the grade of iron is lower than that of Example 1 was able to be obtained.

Example 4

Various impurities were added as reagents, if needed, as in Example 1 to the post-sulfuration liquid having the composition shown in Table 1 above as used in Example 1, and ion exchange treatment with a chelating resin was further performed according to the same approach, and sulfuric acid was passed through the chelating resin after the ion exchange treatment to obtain a scandium eluate having a composition shown in Table 9 above.

The resulting scandium eluate was placed in a container, and a 4 N sodium hydroxide solution was then added with stirring to perform the first stage of neutralization in which the pH was adjusted to 4. Then, solid-liquid separation was performed using a filter paper and a nutsche to obtain a primary neutralized precipitate and a primary neutralized filtrate. Subsequently, the rate (partitioning) of the amount of a precipitate formed to the amount contained in the scandium eluate (Table 9) before the pH adjustment, i.e., the precipitation rate (%) was analyzed by ICP.

Table 11 below shows the precipitation rates (partitioning) from the first stage of neutralization. As shown in Table 11, iron and chromium as impurities in the solution were able to be effectively precipitated by performing neutralization until the pH of the solution became 4, and were able to be separated from scandium which was partitioned into the primary neutralized filtrate.

TABLE 11

| Precipitation rates of each element component | Sc | Al | Fe | Ni | Cr |
|---|---|---|---|---|---|
| [%] | 4 | 4 | 89 | 0 | 50 |

Next, the resulting primary neutralized filtrate was placed in a container, to which 4 N sodium hydroxide was added to perform the second stage of neutralization in which the pH was adjusted to 6. Then, solid-liquid separation was performed as in the first stage of neutralization to obtain a secondary neutralized precipitate and a secondary neutralized filtrate. Subsequently, the rate (partitioning) of the amount of a precipitate formed to the amount contained in the primary neutralized filtrate, i.e., the precipitation rate (%) was analyzed by ICP.

Table 12 below shows the precipitation rates (partitioning) by the second stage of neutralization. As shown in Table 12, almost 90% of scandium mostly remained in the filtrate without precipitating in the first stage of neutralization was partitioned into the secondary neutralized precipitate by the second stage of neutralization. In contrast, nickel which is more basic than scandium did not precipitate during either the first or second stage of neutralization, and remained in the secondary neutralized filtrate, and thus was able to be effectively separated from scandium.

TABLE 12

| Precipitation rates of each element component | Sc | Al | Fe | Ni | Cr |
|---|---|---|---|---|---|
| [%] | 88 | 99 | 99 | 4 | 94 |

Note that among the components in the scandium eluate shown in Table 9, a large amount of iron and chromium also precipitate in the second stage of neutralization, but most of them have already partitioned into the primary neutralized precipitate in the first stage of neutralization, and have been separated from scandium. Therefore, the amount to be partitioned into the secondary neutralized precipitate itself is reduced.

With reference to the rates (the precipitation rates) of the components partitioned into the secondary neutralized precipitate by performing the two-stage neutralization treatment relative to those contained in the scandium eluate as shown in Table 13 below, aluminum is found to be significantly precipitated other than scandium, and iron, chromium, nickel and others are found to be separated effectively.

TABLE 13

| Precipitation rates of each element component | Sc | Al | Fe | Ni | Cr |
|---|---|---|---|---|---|
| [%] | 82 | 99 | 6 | 4 | 31 |

Next, a 2 N sulfuric acid solution was added to the resulting secondary neutralized precipitate, and dissolution was performed while maintaining the pH at around 1 to obtain a re-dissolved liquid as shown in Table 14 below.

TABLE 14

| Re-dissolved liquid | Sc | Al | Fe |
|---|---|---|---|
| [g/L] | 20 | 7.2 | 0.6 |

Next, the resulting re-dissolved liquid as an extraction starting liquid was subjected to solvent extraction as in Example 1, and scandium oxalate was formed from the resulting raffinate liquid, and roasting was then performed to obtain scandium oxide. As a result, scandium oxide in which the grade of iron is lower than that of Example 1 was able to be obtained.

Example 5

Various impurities were added as reagents, if needed, as in Example 1 to the post-sulfuration liquid having the composition shown in Table 1 above as used in Example 1, and ion exchange treatment with a chelating resin was further performed according to the same approach, and sulfuric acid was passed through the chelating resin after the ion exchange treatment to obtain a scandium eluate. Then, the scandium eluate was subjected to two-stage neutralization treatment as described in Example 4, and the resulting re-dissolved liquid as an extraction starting liquid is then subjected to solvent extraction to obtain a raffinate liquid having a composition shown in Table 15 below.

TABLE 15

| Composition of raffinate liquid | Sc | Fe | Al | Ni | Cr |
|---|---|---|---|---|---|
| [g/L] | 10.0 | 0.4 | 2.5 | 0.07 | 0.08 |

Next, sulfuric acid was added to the resulting raffinate liquid as an oxalate-formation starting liquid to adjust the pH of the solution to 0, and maintained at a temperature in the range of the room temperature of 25° C. to 30° C. Note that the pH value of the oxalate-formation starting liquid before the pH adjustment was 1, and the oxidation-reduction potential (ORP) was in the range of 500 mV to 550 mV as measured using a silver-silver chloride electrode as the reference electrode.

Next, oxalic acid was mixed with the oxalate-formation starting liquid after the pH adjustment to perform the oxalate-formation treatment. Here, in general, a reagent is usually added to and mixed with the solution to allow a reaction to occur. Accordingly, crystals or a solution of oxalic acid is conventionally added to the oxalate-formation starting liquid in the oxalate-formation treatment. But, a method of addition opposite to the conventional method was used in the present Example; i.e., an oxalate-formation starting liquid was added to a reaction vessel filled with an oxalic acid solution having an oxalic acid concentration of 100 g/L, the amount of the oxalate-formation starting liquid being in the range between 1.4 equivalence and 2.0 equivalence of scandium contained in the oxalate-formation starting liquid to be added; and allowed to react at the room temperature over 1 hour with stirring.

The resulting precipitate was filtered and separated into a precipitate and a filtrate after performing the oxalate-formation treatment as described above. The separated precipitate was washed with water, and vacuum dried to obtain crystals of scandium oxalate. The resulting crystals of scandium oxalate were roasted as in Example 1 to obtain scandium oxide ($Sc_2O_3$).

The resulting scandium oxide was washed with pure water, and dried, and then analyzed for the metal components by ICP atomic absorption spectroscopy. Measurement results are shown in Table 16 below.

TABLE 16

| Addition equivalence | 1.4 | 1.6 | 1.8 | 2.0 |
|---|---|---|---|---|
| Scandium oxide recovered [%] | 99.94 | 99.92 | 99.93 | 99.92 |
| Fe [ppm] | 14 | 29 | 43 | 29 |
| Al [ppm] | 9 | 9 | 13 | 9 |

As shown in Table 16, the grades of iron and aluminum in scandium oxide were able to be reduced to low levels, and high purity scandium oxide containing scandium with a grade of more than 99.9% was able to be obtained. Further, the grade of uranium was 1 ppm or less of the detection limit.

Reference Example 1

Sulfuric acid was added the same oxalate-formation starting liquid as used in Example 5 to adjust the pH of the solution to 0. In this Reference Example, the oxalic acid solution was added to a container filled with the oxalate-formation starting liquid to effect a reaction when performing the oxalate-formation treatment. Then, the resulting scandium oxalate was roasted in a similar manner, and washed to form scandium oxide, and analyzed for the metal components by ICP atomic absorption spectroscopy. Measurement results are shown in Table 17 below.

TABLE 17

| Addition equivalence | 1.5 | 1.6 | 1.7 |
|---|---|---|---|
| Scandium oxide recovered [%] | 99.93 | 99.84 | 99.86 |
| Fe [ppm] | 99 | 99 | 86 |
| Al [ppm] | 9 | 19 | 19 |

As shown in Table 17, the grades of iron were particularly high as compared with those in scandium oxide obtained from Example 5. As a result, the purity was somewhat decreased; for example, some of the grades of scandium oxide were less than 99.9%.

Reference Example 2

The oxalate-formation treatment was performed as in Example 5 using the same oxalate-formation starting liquid as used in Example 5 except that the pH was left to 1 without performing the pH adjustment with sulfuric acid. The resulting scandium oxide was roasted in a similar manner, and dried, and then analyzed for the metal components by ICP atomic absorption spectroscopy. Measurement results are shown in Table 18 below.

TABLE 18

| Addition equivalence | 1.6 | 1.8 | 2.1 |
|---|---|---|---|
| Scandium oxide recovered [%] | 99.85 | 99.86 | 99.86 |
| Fe [ppm] | 86 | 100 | 86 |
| Al [ppm] | 440 | 270 | 270 |

As shown in Table 18, the grades of iron and aluminum were high as compared with those in scandium oxide obtained from Example 5. As a result, the grades of scandium oxides were less than 99.9%.

The invention claimed is:

1. A method of recovering scandium, comprising: passing a scandium and actinoid element-containing solution through an ion exchange resin; then subjecting an eluent that has been eluted from the ion exchange resin to solvent extraction to allow separation into a raffinate liquid and a post-extraction extractant; then adding oxalic acid to the raffinate liquid to obtain a precipitate of scandium oxalate; and roasting the precipitate to obtain scandium oxide,
   wherein the scandium and actinoid element-containing solution to be subjected to the solvent extraction is a post-sulfuration liquid obtained by hydrometallurgy of nickel oxide ore, the hydrometallurgy comprising:
   a leaching step of leaching the nickel oxide ore with sulfuric acid under high temperature and high pressure to obtain a leachate;
   a neutralization step of adding a neutralizing agent to the leachate to obtain a neutralized precipitate containing impurities and a post-neutralization liquid; and
   a sulfuration step of adding a sulfurizing agent to the post-neutralization liquid to obtain nickel sulfide and a post-sulfuration liquid, and
   wherein an amine-based extractant is used as an extractant for the solvent extraction.

2. The method of recovering scandium according to claim 1, comprising: performing scrubbing, the scrubbing comprising mixing a washing liquid with the extractant after the solvent extraction to separate scandium contained in the extractant into the washing liquid, the washing liquid comprising a sulfuric acid solution having a concentration between 1.0 mol/L or more and 3.0 mol/L or less; and recovering scandium from the washing liquid after the scrubbing.

3. The method of recovering scandium according to claim 1, comprising adding a carbonate salt to the extractant after the solvent extraction to perform backward extraction, thereby obtaining a post-backward extraction extractant and a backward extraction liquid.

4. The method of recovering scandium according to claim 3, wherein the post-backward extraction extractant is repeatedly used as the extractant for the solvent extraction.

5. The method of recovering scandium according to claim 1, comprising: adding a neutralizing agent to the eluent that has been eluted from the ion exchange resin to adjust pH to the range of 5 to 6; performing solid-liquid separation to obtain a neutralized precipitate and a neutralized filtrate; and subjecting a re-dissolved liquid obtained by adding an acid to the neutralized precipitate to the solvent extraction.

6. The method of recovering scandium according to claim 1, comprising: adding a neutralizing agent to the eluent that has been eluted from the ion exchange resin to adjust pH to the range of 3.5 to 4.5; performing solid-liquid separation to obtain a primary neutralized precipitate and a primary neutralized filtrate; then further adding the neutralizing agent to the primary neutralized filtrate to adjust pH to the range of 5.5 to 6.5; performing solid-liquid separation to obtain a secondary neutralized precipitate and a secondary neutralized filtrate; subjecting a re-dissolved liquid obtained by adding an acid to the secondary neutralized precipitate to the solid-liquid separation.

7. The method of recovering scandium according to claim 1, comprising: upon performing the oxalate-formation treatment of the raffinate liquid to obtain the precipitate of scandium oxalate, adjusting the pH of the raffinate liquid to the range of −0.5 to less than 1; adding the solution after the pH adjustment to an oxalic acid-containing solution to generate a precipitate of scandium oxalate.

8. The method of recovering scandium according to claim 2, wherein the scandium and actinoid element-containing solution to be subjected to the solvent extraction is a post-sulfuration liquid obtained by hydrometallurgy of nickel oxide ore, the hydrometallurgy comprising:
  a leaching step of leaching the nickel oxide ore with sulfuric acid under high temperature and high pressure to obtain a leachate;
  a neutralization step of adding a neutralizing agent to the leachate to obtain a neutralized precipitate containing impurities and a post-neutralization liquid; and
  a sulfuration step of adding a sulfurizing agent to the post-neutralization liquid to obtain nickel sulfide and a post-sulfuration liquid.

9. The method of recovering scandium according to claim 3, wherein the scandium and actinoid element-containing solution to be subjected to the solvent extraction is a post-sulfuration liquid obtained by hydrometallurgy of nickel oxide ore, the hydrometallurgy comprising:
  a leaching step of leaching the nickel oxide ore with sulfuric acid under high temperature and high pressure to obtain a leachate;
  a neutralization step of adding a neutralizing agent to the leachate to obtain a neutralized precipitate containing impurities and a post-neutralization liquid; and
  a sulfuration step of adding a sulfurizing agent to the post-neutralization liquid to obtain nickel sulfide and a post-sulfuration liquid.

10. The method of recovering scandium according to claim 4, wherein the scandium and actinoid element-containing solution to be subjected to the solvent extraction is a post-sulfuration liquid obtained by hydrometallurgy of nickel oxide ore, the hydrometallurgy comprising:
  a leaching step of leaching the nickel oxide ore with sulfuric acid under high temperature and high pressure to obtain a leachate;
  a neutralization step of adding a neutralizing agent to the leachate to obtain a neutralized precipitate containing impurities and a post-neutralization liquid; and
  a sulfuration step of adding a sulfurizing agent to the post-neutralization liquid to obtain nickel sulfide and a post-sulfuration liquid.

11. The method of recovering scandium according to claim 2, comprising: adding a neutralizing agent to the eluent that has been eluted from the ion exchange resin to adjust pH to the range of 5 to 6; performing solid-liquid separation to obtain a neutralized precipitate and a neutralized filtrate; and subjecting a re-dissolved liquid obtained by adding an acid to the neutralized precipitate to the solvent extraction.

12. The method of recovering scandium according to claim 3, comprising: adding a neutralizing agent to the eluent that has been eluted from the ion exchange resin to adjust pH to the range of 5 to 6; performing solid-liquid separation to obtain a neutralized precipitate and a neutralized filtrate; and subjecting a re-dissolved liquid obtained by adding an acid to the neutralized precipitate to the solvent extraction.

13. The method of recovering scandium according to claim 4, comprising: adding a neutralizing agent to the eluent that has been eluted from the ion exchange resin to adjust pH to the range of 5 to 6; performing solid-liquid separation to obtain a neutralized precipitate and a neutralized filtrate; and subjecting a re-dissolved liquid obtained by adding an acid to the neutralized precipitate to the solvent extraction.

14. The method of recovering scandium according to claim 2, comprising: adding a neutralizing agent to the eluent that has been eluted from the ion exchange resin to adjust pH to the range of 3.5 to 4.5; performing solid-liquid separation to obtain a primary neutralized precipitate and a primary neutralized filtrate; then further adding the neutralizing agent to the primary neutralized filtrate to adjust pH to the range of 5.5 to 6.5; performing solid-liquid separation to obtain a secondary neutralized precipitate and a secondary neutralized filtrate; subjecting a re-dissolved liquid obtained by adding an acid to the secondary neutralized precipitate to the solid-liquid separation.

15. The method of recovering scandium according to claim 3, comprising: adding a neutralizing agent to the eluent that has been eluted from the ion exchange resin to adjust pH to the range of 3.5 to 4.5; performing solid-liquid separation to obtain a primary neutralized precipitate and a primary neutralized filtrate; then further adding the neutralizing agent to the primary neutralized filtrate to adjust pH to the range of 5.5 to 6.5; performing solid-liquid separation to obtain a secondary neutralized precipitate and a secondary neutralized filtrate; subjecting a re-dissolved liquid obtained by adding an acid to the secondary neutralized precipitate to the solid-liquid separation.

16. The method of recovering scandium according to claim 4, comprising: adding a neutralizing agent to the eluent that has been eluted from the ion exchange resin to adjust pH to the range of 3.5 to 4.5; performing solid-liquid separation to obtain a primary neutralized precipitate and a primary neutralized filtrate; then further adding the neutralizing agent to the primary neutralized filtrate to adjust pH to the range of 5.5 to 6.5; performing solid-liquid separation to obtain a secondary neutralized precipitate and a secondary neutralized filtrate; subjecting a re-dissolved liquid obtained by adding an acid to the secondary neutralized precipitate to the solid-liquid separation.

17. The method of recovering scandium according to claim 2, comprising: upon performing the oxalate-formation treatment of the raffinate liquid to obtain the precipitate of scandium oxalate, adjusting the pH of the raffinate liquid to the range of −0.5 to less than 1; adding the solution after the pH adjustment to an oxalic acid-containing solution to generate a precipitate of scandium oxalate.

18. The method of recovering scandium according to claim 3, comprising: upon performing the oxalate-formation treatment of the raffinate liquid to obtain the precipitate of scandium oxalate, adjusting the pH of the raffinate liquid to the range of −0.5 to less than 1; adding the solution after the pH adjustment to an oxalic acid-containing solution to generate a precipitate of scandium oxalate.

19. The method of recovering scandium according to claim 4, comprising: upon performing the oxalate-formation treatment of the raffinate liquid to obtain the precipitate of scandium oxalate, adjusting the pH of the raffinate liquid to the range of −0.5 to less than 1; adding the solution after the pH adjustment to an oxalic acid-containing solution to generate a precipitate of scandium oxalate.

* * * * *